United States Patent [19]

Zielske et al.

[11] Patent Number: 5,049,305

[45] Date of Patent: Sep. 17, 1991

[54] PHENOXYACETATE PERACID PRECURSORS AND PERHYDROLYSIS SYSTEMS THEREWITH

[76] Inventors: Alfred G. Zielske, 2282 Via Espada, Pleasanton, Calif. 94566; Ronald A. Fong, 513 Avanel Dr., Modesto, Calif. 95356

[21] Appl. No.: 543,344

[22] Filed: Jun. 25, 1990

Related U.S. Application Data

[60] Division of Ser. No. 353,970, May 19, 1989, Pat. No. 4,956,117, which is a division of Ser. No. 45,197, Apr. 30, 1987, Pat. No. 4,859,800, which is a continuation-in-part of Ser. No. 927,856, Nov. 6, 1986, abandoned.

[51] Int. Cl.$^5$ .................. C09K 3/00; C07C 69/76
[52] U.S. Cl. ................ 252/186.38; 252/186.39; 252/186.25; 560/61
[58] Field of Search .............. 252/186.38, 186.39, 252/186.25, 95; 548/545; 560/61; 562/2; 568/566

[56] References Cited

U.S. PATENT DOCUMENTS

| | | | |
|---|---|---|---|
| 2,898,181 | 8/1959 | Dithmar et al. | 8/137 |
| 3,061,550 | 10/1962 | Baevsky | 252/99 |
| 3,075,921 | 1/1963 | Brocklehurst et al. | 252/99 |
| 3,130,165 | 4/1964 | Brocklehurst | 252/99 |
| 3,163,606 | 12/1964 | Viveen et al. | 252/98 |
| 3,637,339 | 1/1972 | Gray | 252/99 |
| 3,655,567 | 4/1972 | Gray | 252/95 |
| 3,816,319 | 6/1974 | Sarot et al. | 252/95 |
| 3,928,223 | 12/1975 | Murray | 252/95 |
| 3,969,257 | 7/1976 | Murray | 252/102 |
| 3,975,153 | 8/1976 | Dounchis et al. | 8/111 |
| 3,996,152 | 12/1976 | Edwards et al. | 252/186 |
| 4,164,395 | 8/1979 | Finley et al. | 8/111 |
| 4,283,301 | 8/1981 | Diehl | 252/102 |
| 4,337,213 | 6/1982 | Marynowski et al. | 260/502 R |
| 4,483,778 | 11/1984 | Thompson et al. | 252/94 |
| 4,486,327 | 12/1984 | Murphy et al. | 252/94 |
| 4,536,314 | 8/1985 | Hardy et al. | 252/102 |
| 4,539,130 | 9/1985 | Thompson et al. | 252/94 |
| 4,606,838 | 8/1986 | Burns | 252/94 |
| 4,681,592 | 7/1987 | Hardy et al. | 252/186.38 |
| 4,956,117 | 8/1990 | Zielski et al. | 252/186.38 |

FOREIGN PATENT DOCUMENTS 0166571 1/1986 European Pat. Off.
8502407 9/1985 Netherlands.

OTHER PUBLICATIONS

Morrison and Boyd, *Organic Chemistry*, pp. 594–595 (1962).
Kirk–Othmer, *Encyclopedia of Chemical Technology*, vol. 11: Fluorine Compounds to Gold and Gold Compounds, pp. 287 and 290.
Aldrich Chemical Company Fine Chemicals, Catalog pp. 1467, 1484 and 1497 (1986).

*Primary Examiner*—Robert L. Stoll
*Assistant Examiner*—Joseph D. Anthony
*Attorney, Agent, or Firm*—Majestic, Parsons, Siebert & Hsue

[57] ABSTRACT

A perhydrolysis system is provided which includes peroxyacid precursors and a source of peroxygen. Upon dissolution in water these compositions provide high yields of a novel peroxyacid having the structure

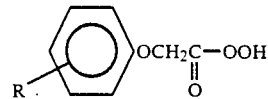

where R is hydrogen or an alkyl of not more than 5 carbon atoms. The precursors may include hydroxyl nitrogen derivatives as leaving groups, since the α-substituted phenoxy moiety enhances carbonyl reactivity toward perhydroxyl anion.

12 Claims, No Drawings

PHENOXYACETATE PERACID PRECURSORS AND PERHYDROLYSIS SYSTEMS THEREWITH

This is a divisional of application Ser. No. 07/353,970, filed May 19, 1989, now U.S. Pat. No. 4,956,117, which is a division of application Ser. No. 07/045,197, filed April 30, 1987, now U.S. Pat. No. 4,859,800 continuation-in-part of 06/927,856 filed Nov. 6, 1986, now abandoned.

FIELD OF THE INVENTION

The present invention relates to peroxyacids, and particularly to α-substituted peroxyacid precursors which will react with peroxide anion in aqueous solution to form the desired peroxyacid in situ.

BACKGROUND OF THE INVENTION

Peroxy compounds are effective bleaching agents, and compositions including mono- or di-peroxyacid compounds are useful for industrial or home laundering operations. For example, U.S. Pat. No. 3,996,152, issued Dec. 7, 1976, inventors Edwards et al., discloses bleaching compositions including peroxygen compounds such as diperizelaic acid and diperisophthalic acid.

Peroxyacids have typically been prepared by the reaction of carboxylic acids with hydrogen peroxide in the presence of sulfuric acid. For example, U.S. Pat. No. 4,337,213, inventors Marynowski et al., issued June 29, 1982, discloses a method for making diperoxyacids in which a high solids throughput may be achieved.

However, granular bleaching products containing peroxyacid compounds tend to lose bleaching activity during storage, due to decomposition of the peroxyacid. The relative instability of peroxyacid presents a problem of storage stability for compositions consisting of or including peroxyacids.

One approach to the problem of reduced bleaching activity of peroxyacid compositions has been to include "activators" for or precursors of peroxyacids. U.S. Pat. No. 4,283,301, inventor Diehl, issued August 11, 1981, discloses bleaching compositions including peroxygen bleaching compounds, such as sodium perborate monohydrate or sodium perborate tetrahydrate, and activator compounds such as isopropenyl hexanoate and hexanoyl malonic acid diethyl ester. However, these bleach activators tend to yield an unpleasant odor under actual wash conditions. U.S. Pat. No. 4,486,327, inventors Murphy et al., issued December 4, 1984, and U.S. Pat. No. 4,536,314, inventors Hardy et al., issued August 20, 1985, disclose certain alpha substituted derivatives of $C_6$-$C_{18}$ carboxylic acids which are said to activate peroxygen bleaches and are said to reduce malodor.

U.S. Pat. No. 4,539,130, inventors Thompson et al., issued September 3, 1985 (and its related U.S. Pat. No. 4,483,778, inventors Thompson et al., issued November 20, 1984) disclose chloro, methoxy or ethoxy subsituted on the carbon adjacent to the acyl carbon atom. U.S. Pat. No. 3,130,165, inventor Brocklehurst, issued April 21, 1964, also discloses an α-chlorinated peroxyacid, which is said to be highly reactive and unstable.

European Patent Application 166,571, inventors Hardy et al., published January 2, 1986, discloses peracids and peracid precursors said to be of the general type RXAOOH and RXAL, wherein R is said to be a hydrocarbyl group, X is said to be a hetero-atom, A is said to be a carbonyl bridging group, and L is a leaving group, such as an oxybenzene sulfonate. $C_6$ through $C_{20}$ alkyl substituted aryl are said to be preferred as R, with $C_6$-$C_{15}$ alkyl said to be especially preferred for oxidative stability.

Various compounds have been disclosed in the prior art that contain nitrogen as part of peroxygen precursor leaving groups. Murray, U.S. Pat. Nos. 3,969,257, Gray, 3,655,567, Baevsky, 3,061,550, and Murray, U.S. Pat. No. 3,928,223 appear to disclose the use of acyl groups attached to nitrogen atoms as leaving groups for activators. In Finley et al., U.S. Pat. No. 4,164,395, a sulfonyl group is attached to the nitrogen atom of the leaving group. The activator structure is thus a sulfonyl oxime. Dounchis et al., U.S. Pat. No. 3,975,153 teaches the use of isophorone oxime acetate as a bleach activator. It is claimed that this isophorone derivative results in an activator of low odor and low toxicity. In Sarot et al., U.S. Pat. Nos. 3,816,319, the use of diacylated glyoximea are taught.

In sum, many different peracid activators or precursors have been proposed. However, there remain a number of problems for commercially feasible applications. Among these problems are that the known peroxygen activators and precursors have been difficult to prepare on a commercial scale, have been made from relatively expensive or toxic raw materials, have tended to yield an unpleasant odor under wash conditions, or have been found to provide impractically low yields of peroxyacid in situ.

SUMMARY OF THE INVENTION

It is an object of the present invention to provide odorless peroxyacid precursors that are readily prepared from relatively inexpensive raw materials, and give excellent yields in situ of peroxyacid when dissolved with a source of peroxide in water.

It is a further object of the present invention to provide a shelf stable, dry bleaching and/or laundering composition that gives effective peroxygen bleaching in laundering operations, even at low temperature wash or bleaching solutions.

These and other objects are provided by the present invention.

In one aspect of the present invention, a perhydrolysis system for in situ generation of peroxyacid comprises: a peroxyacid precursor which includes at least one α-substituted carbonyl moiety with the structure

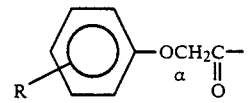

wherein R is hydrogen or a alkyl with 5 or less carbon atoms; and, a source of peroxygen which will react with the peroxyacid precursor in aqueous solution to form a peroxyacid having the structure

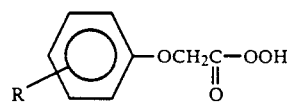

The inventive perhydrolysis system preferably provides yields of at least about 75% of peroxyacid from the peroxyacid precursor at pH 9.5, even at low wash temperatures such as 21° C., and provides considerable flexibility in the choice of particular leaving group.

It is believed that the phenoxy moiety, which is substituted on the α-carbon of the acetate moiety, enhances the overall reactivity toward the perhydroxyl anion. It is believed that this enhanced reactivity permits the flexibility of choice for leaving groups. Thus, peroxyacid precursors of the invention may be prepared with derivatives of oximes, N-hydroxyimides or amine oxides as leaving groups. These hydroxyl nitrogens are less expensive than phenol sulfonates, and can provide better storage stability for the peroxyacid precursors including such hydroxyl nitrogen derivatives. Substituted or unsubstituted phenol derivatives as leaving groups are also within the scope of the invention.

DETAILED DESCRIPTION OF THE PREFERRED EMBODIMENTS

One aspect of the present invention is a perhydrolysis system for in situ generation of certain peroxyacids. By "perhydrolysis" is meant the reaction of a selected peroxyacid precursor with peroxide to form a peroxyacid. This reaction is in situ in that it occurs when the peroxyacid precursor is dissolved in sufficient water along with the source of peroxide. It is important that the perhydrolysis reaction be substantially complete within not more than about five minutes even at relatively low temperatures, to permit sufficient bleaching time during a normal washing machine wash cycle.

Normally, when the conjugate acids of leaving groups have a relatively high $pK_a$ (on the order of 11–13), then there would not be sufficient reactivity to provide adequate perhydrolysis. However, having the α-phenoxy substituent enhances reactivity such that even relatively high $pK_a$'s of 11 to about 13 provide precursors of the invention with excellent yields of peroxyacid. The structure of the peroxyacid formed is shown by Formula I. The detection and quantitative determination of the inventive peroxyacid illustrated by Formula I was done according to the procedure outlined in *Organic Peroxides*, Vol. I, Daniel Swern, Editor, Wiley-Interscience, New York (1970), p. 501.

Formula I

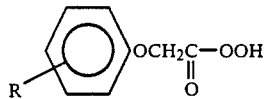

The peroxyacid precursors of the invention yielding the Formula 1 peroxyacid will sometimes be referred to as phenoxyacetate peroxyacid precursors. This is because these inventive precursors may be viewed as α-substituted, acetic acid analogs with the α-substituent being a phenoxy moiety. This phenoxy moiety may have an alkyl substituent (branched or straight) of not more than 5 carbon atoms. Thus, the R substituent shown in Formula 1 and throughout this specification may be hydrogen or, as just explained, an alkyl of not more than 5 carbon atoms. Such peroxyacid precursors include at least one α-substituted carbonyl moiety with the structure illustrated by Formula II, where L is a leaving group.

Formula II

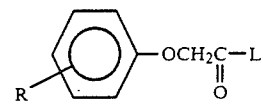

The carbonyl carbon of Formula II is preferably esterified, and will have the leaving group bonded through the ester linkage. Suitable leading groups will be exemplified hereinafter.

The α-position substitution is important. For example, if one were to substitute the phenoxy group directly to the carbonyl carbon, then an undesired peroxyacid could be formed as a consequence of the phenoxy acting as a leaving group rather than an esterified, desired leaving group. For another example, if one were to substitute the phenoxy at the β-position, then the variety of choice for suitable leaving groups would be greatly diminished.

The α-substituted carbonyl moiety illustrated by Formula II can be prepared from readily available starting materials such as phenol and chloroacetic acid, as generally illustrated by Reaction Scheme I, to form a phenoxyacetic acid to which a leaving group will then be bonded.

Reaction Scheme I

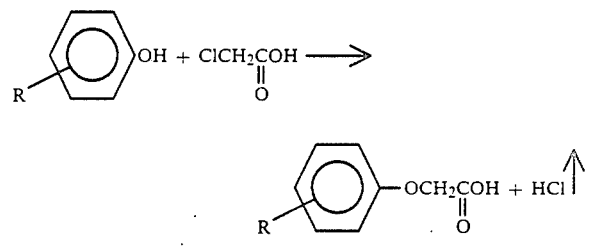

A variety of leaving groups may then be included in the phenoxyacetic acid molecule, usually by a condensation reaction, to yield the resultant peroxyacid precursor. Suitable leaving groups include derivatives of substituted or unsubstituted phenols, oximes, N-hydroxyimides, and amine oxides. It has been discovered that the oxime, N-hydroxyimide and amine oxide derivatized leaving groups are also useful in certain other peroxygen bleach compositions, as described in copending Application Ser. No. 928,065, inventor Zielske, filed November 6, 1986, entitled "ACYLOXYNITROGEN PERACID PRECURSORS", of common assignment herewith, and in copending application Ser. No. 928,070, inventors Fong et al., filed November 6, 1986, now U.S. Pat. No. 4,778,618, issued Oct. 18, 1988 entitled "GLYCOLATE ESTER PERACID PRECURSORS", also of common assignment herewith.

A particularly preferred unsubstituted phenol for this invention is resorcinol, although other dihydroxybenzenes (e.g. hydroquinone) are feasible for derivatization in forming these peroxyacid precursors.

Substituted phenols may be substituted with solubilizing groups, such as carbonate, sulfonate, sulfate and quarternary nitrogen, and/or may be substituted with straight or branched chain alkyls with about 1 to 6 carbons or alkoxys with about 1 to 10 carbons. Illustrated substituted phenols include p-phenolsulfonic acids and salts thereof, o-phenolsulfonic acids and salts thereof, p- and o-hydroxybenzoic acids and salts thereof, 4-(trimethylammonium chloride)-phenol, 4-(trimethylammonium bromide)-phenol, 4-(trimethylammonium hydroxide)-phenol and 4-(trimethylammonium iodide)phenol.

Oximes of aldehydes or ketones are suitable in forming the leaving group, and illustrative oximes include acetaldoxime, benzaldoxime, propionaldoxime, butyaldoxime, heptaldoxime, hexaldoxime, phenylaetald oxime, p-tolualdoxime, anisaldoxime, carpoaldoxime, valeraldoxime, p-nitrobenzaldoxime, acetone oxime, methyl ethyl ketoxime, 2-pentanone oxime, 2-hexanone oxime, 3-hexanoneoxime, cyclohexanone oxime, acetophenone oxime, benzophenone oxime, and cyclopentanone oxime.

Illustrative N-hydroxyimides include N-hydroxysuccinimide, N-hydroxy phthalimide, N-hydroxy glutarimide, N-hydroxy napthalimide, N-hydroxy maleimide, N-hydroxy diacetylimide and N-hydroxy diproprionylimide.

Illustrative amine oxides include pyridine N-oxide, 3-picoline N-oxide, trimethylamine N-oxide, 4-phenyl pyridine N-oxide, decyldimethylamine N-oxide, dodecyl dimethylamine N-oxide, tetradecyl dimethylamine N-oxide, hexadecyl dimethylamine N-oxide, octyl dimethylamine N-oxide, di(decyl)methylamine N-oxide, di(dodecyl)methylamine N-oxide, di(tetradecyl)methylamine N-oxide, 4-picoline N-oxide, and 2-picoline N-oxide.

Particularly preferred peroxyacid precursors with an unsubstituted phenol derivative as leaving group are illustrated by Formulas III.

Formulas III

[Chemical structure: R—C6H4—OCH2C(=O)—O—C6H5]

[Chemical structure: C6H5—OCH2C(=O)—O—C6H4—OCCH2O—C6H5]

Particularly preferred peroxyacid precursors with a substituted phenol as leaving group are illustrated by Formula IV, where $R_2$ is hydrogen, a straight or branched alkyl with about 1–6 carbons, or an alkoxy with about 1–10 carbons, and $Y_2$ is a hydrogen sulfonate, a sulfate, a quarternary nitrogen, or a carbonate.

Formula IV

[Chemical structure: R—C6H4—OCH2C(=O)—O—C6H3(Y2)(R2)]

Particularly preferred peroxyacid precursors with hydroxyl nitrogen derivatives as leaving group include structures illustrated by Formulas V, VI and VII. In Formula V, $R_3$ and $R_4$ are each straight or branched chain alkyl groups with 1 to 6 carbons, or may include a lower alkyl substituted aryl. The $R_4$ substituent of Formulas VI may be an aromatic ring and the $R_5$ and $R_6$ substituents are straight or branched hydrocarbons with about 1 to 6 carbons. In Formulas VII, $R_8$ and $R_9$ may be the same or different and are preferably $C_1$–$C_{20}$ alkyl, aryl, or alkalaryl. If alkyl, the substituent could be partially unsaturated. The dotted lines illustrate that $R_8$ and $R_9$ may be part of the same aromatic or cycloalkyl ring. Formula V illustrates inventive precursors derived from oximes. Formulas VI illustrate inventive precursors derived from N-hydroxyimides, and Formulas VII illustrate inventive precursors derived from amine oxides.

Formula V

[Chemical structure: R—C6H4—OCH2C(=O)—ON=CR3R4]

Formulas VI

[Chemical structure: R—C6H4—OCH2CON(succinimide ring)—R5 OR]

[Chemical structure: R—C6H4—OCH2CON(ring with R6, R7)]

Formula VII

[Chemical structure: R—C6H4—OCH2CON with C—R8, C—R9 and H(1 or 2)]

The phenoxyacetic acid illustrated by Reaction Scheme I may be esterified to include the desired leaving group in a number of conventional ways: by treatment of the acid with an alcohol (or phenol) under usual acid catalyzed conditions, or by conversion of the phenoxy-acetic acid to an acid chloride, followed by treatment with an alcohol (or phenol).

A preferred condensation reaction to form a peroxyacid precursor having a sulfonated phenyl leaving group is generally illustrated by Reaction Scheme II.

Reaction Scheme II

[Chemical scheme: R—C6H4—OCH2C(=O)—OH + R1C=O + R1C=O (anhydride)]

$HO\phi SO_3M \xrightarrow{(solvent)}$

[Chemical structure: R—C6H4—OCH2CO—C6H4—SO3M + HOCR1↑]

Reaction Scheme II is preferably performed from an initial reaction mixture including four essential components: the phenoxyacetic acid, preferably obtained from Reaction Scheme I; a phenol sulfonate; a lower alkyl acid anhydride; and, an alkyl hydrocarbon solvent. The initial reaction mixture is heated and refluxed for a sufficient time to form an acid by-product which is removed by distillation. The sulfonated phenyl ester reaction product (i.e., as inventive peroxyacid precursor) is formed in this preferred, one-pot synthesis. Such a synthesis is described in pending U.S. patent ppplication Ser. No. 915,133, filed October 3, 1986, now U.S. Pat. No. 4,735,740, issued Apr. 5, 1988 entitled "DIPEROXYACID PRECURSORS AND METHOD", of common assignment herewith, and incorporated by reference herein. Example I also particularly describes such a reaction.

When a hydroxyl nitrogen compound is utilized in forming the leaving group of the peroxyacid precursor, then a condensation reaction the same as or analogous to Examples III–VII may be performed.

The phenoxyacetate peroxyacid precursors of the invention permit considerable flexibility in choice of leaving groups, as they give enhanced amounts of peroxyacid with respect to precursors without the necessary α-phenoxy substitution. This is illustrated by the excellent perhydrolysis of three peroxyacid precursors of this invention with three different leaving groups (the preparations of which are more fully described in Examples II, III and IA, respectively). These three inventive peroxy precursors were each dissolved (with the aid of surfactant, if necessary) in a 0.02M carbonate buffer, pH 10.5, 21° C., in a 2:1 ratio of peroxide source to ester group, and then each tested for yield of peroxyacid after five minutes. Each solution was calculated as providing a theoretical 14 ppm A.0. The results are set out in Table I.

TABLE I

| Compound Structure | % Perhydrolysis |
|---|---|
| Inventive Composition (1) $\bigcirc\!-\!OCH_2C(=\!O)\!-\!O\!-\!\bigcirc\!-\!OCCH_2O(=\!O)\!-\!\bigcirc$ | 97 |
| Inventive Composition (2) $\bigcirc\!-\!OCH_2CON\!=\!C(CH_3)_2$ with C=O | 86 |
| Inventive Composition (3) $\bigcirc\!-\!OCH_2CO(=\!O)\!-\!\bigcirc\!-\!SO_3Na$ | 92 |

As can be seen from the data of Table I, Inventive Composition (1), which illustrates a peroxyacid precursor of the invention including two α-substituted carbonyl moieties and a derivatized resorcinol bridge, provides 97% hydrolysis. By contrast, a compound was prepared with the same derivatized resorcinol bridge, but without the α- phenoxy substituent, was tested in an analogous manner, and was found to provide less than 10% perhydrolysis.

It has been found that an unsubstituted ring of the phenoxy moiety gives better perhydrolysis performance than a hydroalkyl substituent on the ring with 6 or 8 carbons, although substituents with up to 5 carbons give excellent perhydrolysis performance also. There is a surprising difference in perhydrolysis performance between compounds of the invention, and compounds with an alkyl substituent on the ring of greater than 5 carbons, as is illustrated by the data of Table II.

The experiment from which the Table II data was taken was performed as follows. The peroxyacid precursors were prepared, and then dissolved (with the aid of surfactant, if necessary) in a 0.02M carbonate buffer, pH 10.5, 21° C., in a 2:1 ratio peroxide source to ester group, and tested for yield of peroxyacid after five minutes. The solutions were prepared by calculating the amount of peroxyacid precursor required to provide a theoretical 14 ppm A.O. Similarly, two comparison compositions (where R was 6 or 8) were prepared and tested.

TABLE II

| Compound Structure | % Perhydrolysis |
|---|---|
| $R\!-\!\bigcirc\!-\!OCH_2C(=\!O)\!-\!O\!-\!\bigcirc\!-\!SO_3Na$ | |
| R = H | 92 |
| R = 4 (tertiary) | 83 |
| R = 5 | 86 |
| R = 6 | 15 |
| R = 8 (tertiary) | 26 |

The dramatically better perhydrolysis of the compounds illustrated in Table II where R is hydrogen, t-butyl or pentyl with respect to the compounds having a hexyl or a t-octyl substituent is particularly surprising because aliphatic peroxyacids with 8 to 12 carbons (with a phenol sulfonate leaving group) give good perhydrolysis.

The peroxyacid precursors are usefully formulated with a solid source of peroxide, such as an alkaline peroxide, in an amount effective to perhydrolyze the peroxyacid precursor, and thus to provide effective bleaching. Suitable sources of peroxide include sodium perborate monohydrate, sodium perborate tetrahydrate, sodium carbonate peroxyhydrate, sodium pyrophosphate peroxyhydrate, urea peroxyhydrate, sodium peroxide, and mixtures thereof. Sodium perborate monohydrate and sodium perborate tetrahydrate are particularly preferred alkaline peroxides for combination with the peroxyacid precursors as a dry bleach composition or, when surfactant is included, as a dry laundering and bleaching composition.

The source of peroxide (that is, compounds yielding hydrogen peroxide in an aqueous solution) itself constitutes a peroxygen bleaching compound. However, bleach compositions including peroxyacid precursor and peroxide source together provide better bleaching, particularly at temperatures below about 60° C., than the peroxide source alone. The range of peroxide to peroxyacid precursor is preferably determined as a molar ratio of peroxide to ester groups contained in the precursor. Thus, with monoester or diester precursors, the range of peroxide to each ester group is a molar ratio of from about 1:1 to 10:1, more preferably about 2:1 to 5:1.

The desirably high perhydrolysis profiles of the inventive perhydrolysis system are coupled with a desirably low to moderate hydrolysis profile. Thus, the inventive perhydrolysis system preferentially forms the desired peroxyacid when dissolved in water.

When phenol sulfonate derivatives are utilized as the leaving group, care should be taken to avoid exposure to moisture during storage prior to use in wash water. This is because such compounds tend to be hygroscopic. One preferred way to solve this potential problem of storage stability is to coat granules of the peroxyacid precursor with one or more of a wide variety of surfactants (e.g. a nonionic surfactant, an anionic surfactant or a cationic surfactant).

When coating with a surfactant, it is preferred to select a surfactant that is solid at room temperatures but melts at temperatures above about 40° C. A melt of surfactant may be simply admixed with peroxyacid precursors, cooled and chopped into granules. Exemplary such surfactants are illustrated in Table III.

TABLE III

| Commercial Name | m.p. | Type | Supplier |
| --- | --- | --- | --- |
| Pluronic F-98 | 55° C. | Nonionic | BASF Wyandotte |
| Neodol 25-30 | 47° C. | Nonionic | Shell Chemical |
| Neodol 25-60 | 53° C. | Nonionic | Shell Chemical |
| Tergitol-S-30 | 41° C. | Nonionic | Union Carbide |
| Tergitol-S-40 | 45° C. | Nonionic | Union Carbide |
| Pluronic 10R8 | 46° C. | Nonionic | BASF Wyandotte |
| Pluronic 17R8 | 53° C. | Nonionic | BASF Wyandotte |
| Tetronic 90R8 | 47° C. | Nonionic | BASF Wyandotte |
| Amidox C5 | 55° C. | Nonionic | Stepan |

Surfactant coatings are also desirable when the peroxyacid precursors include leaving groups other than phenol sulfonate derivatives (e.g. derivatized oximes, N-hydroxyimides and the like) to ensure that the peroxyacid precursor is solubilized fully in aqueous solution during an early part of the wash cycle.

Peroxyacid precursors of the invention dissolved in sufficient water along with a source of peroxide give excellent stain removal. Thus, diagnostic evaluations of oxidant performance were performed with 100% cotton swatches stained with crystal violet as follows. Crystal violet (0.125 g) was added to 1.25 liters of distilled water. Two-inch x two-inch undyed, 100% cotton swatches were added to the solution and agitated for eight hours. The cotton swatches (now dyed with crystal violet) were removed from the staining solution and rinsed repeatedly with cold tap water until the effluent was nearly clear and allowed to air dry. All swatches were read pre- and post-wash on a Hunter Spectrocolorimeter set at 10°, illuminant D. Treatments that included detergent were read with Uv filters in place. Experiments were carried out in beakers with five swatches in 200 ml of solution. The solutions were stirred on a magnetic stir plate. Respective peracide precursors and hydrogen peroxide were allowed to dissolve for 30 seconds before swatches were added. At the end of a ten-minute wash, the swatches were rinsed under the deionized water tap and then air dried.

Three peroxyacids of the invention were used to wash such stained cotton swatches, and the stain removal performances were evaluated. The performance results are summarized in Table IV.

TABLE IV

| Precursor Structure | % Stain Removal (14 ppm A.O.) |
| --- | --- |
| 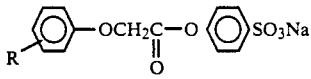 | |
| R = H | 97 |
| R = 4 (tertiary) | 94 |
| R = 5 | 92 |

By contrast, hydrogen peroxide alone (in sufficient quantity to provide 28 ppm) provided only 32% stain removal. This illustrates that the perhydrolysis system provides better bleaching than the peroxide source alone, although hydrogen peroxide by itself constitutes a peroxygen bleaching compound.

When the bleaching compositions are also laundering compositions (that is, are admixed with detergent in addition to or without the earlier described surfactant coating), then it is preferred that the amount of perhydrolysis system, or peroxygen bleach composition in such a combination, be from about 1 wt. % to about 20 wt. % of the total composition, and preferably from about 5 wt. % to about 10 wt. %.

The peroxygen bleach composition (including the peroxyacid precursor and a source of peroxide), when used as a bleaching and laundering composition, may be formulated with a wide variety of different detergents, and the well known dry anionic, cationic, non-ionic, ampholytic or zwitterionic detergents, or mixtures of such detergents, are suitable. A few examples are described below.

Useful anionic detergents include, for example, the water-soluble salts (e.g., alkali metal, ammonium and alkyl ammonium salts) of organic sulfuric reaction products having in their molecular structure an alkyl group containing from about 10 to about 20 carbon atoms and a sulfonic acid or sulfuric acid ester group, such as the sodium and potassium alkyl sulfates and the alkyl benzene sulfonates.

Suitable nonionic detergent for use in a dry laundering composition of the invention include the polyethylene oxide condensates of alkyl phenols, the condensation products of aliphatic alcohols with from about 1 to about 25 moles of ethylene oxide, and the like.

Suitable zwitterionics include derivatives of secondary and tertiary amines, derivatives of heterocyclic secondary and tertiary amines, or derivatives of quaternary ammonium, quaternary phosphonium or tertiary sulfonium compounds.

Useful cationics include the alkyl quaternary ammonium surfactants.

Compositions in accordance with the invention may also include one or more laundry adjuvants such as detergent builders, buffering agents, enzymes, and minor amounts of other water-soluble solid materials such as wetting agents, dyes and perfumes. Buffering agents can be utilized to maintain an alkaline pH of the bleaching and/or laundering solutions, since the peroxygen bleach composition of the invention is most effective at a pH of about 9.0 to about 10.5.

Some of the peroxyacetate peroxy precursors are solid and others liquid at ambient temperatures The liquid precursors may be packaged in one compartment of a dual dispensing device, such as described in U.S. Pat. No. 4,585,150, inventors Beacham et al., issued Apr. 29, 1986, with the source of peroxide (liquid or solid) in the other compartment. Alternatively, the liquid precursors may be dissolved in a volatile non-nucleophilic solvent (such as an alcohol, acetone, a low molecular weight hydrocarbon, or the like) and sprayed onto an inert, solid substrate (such as sodium chloride, sodium sulfate, sodium borate or a zeolite).

Examples IA-B through VII illustrate preparations of inventive embodiments.

EXAMPLE IA

A five-liter three-neck Morton flask was equipped with a paddle stirrer, condenser, drying tube and heating mantle. Into this flask was added 1400 ml Isopar M (isoparaffinic solvent available from Exxon Corporation) and heated to about 150°–160° C. To this was added acetic anhydride (243 g), p-phenol sulfonate (414 g), sodium acetate (10 g) and phenoxyacetic acid (304 g). This mixture was stirred very rapidly and kept at the elevated temperature overnight. A Dean-Stark trap was added between the reaction flask and condenser, and a thermometer was added to the flask. The acetic acid byproduct was removed until the temperature rose to 206° C. (the initial temperature was 146° C. when distillate began to appear in the Dean-Stark trap).

The reaction mixture was allowed to cool and was filtered to give a tan solid. The solid was washed with ether (about 800 ml) on the filter pad. The solid was transferred to a two-liter flask, ether (about 700 ml) added, was stirred, refiltered, and air dried. The crude reaction product showed very little hydroxyl with IR analysis and a carbonyl at 1780 cm$^{-1}$. The crude, air dried material gave 731.2 g of solid. This crude material was then purified and analyzed by several techniques.

The crude solid was dissolved in hot H$_2$O/MeOH (50/50 v/v, 3,000 ml), then stirred in a five-liter Morton flask in an ice-bath until the internal temperature was 7° C. The resulting thick slurry was filtered, and then let air dry overnight. The purified dried (vacuum oven, 110° C.) solid showed no hydroxyl by IR and showed two carbonyls at 1760 cm$^{-1}$ and 1790 cm$^{-1}$ HPLC showed 98.7% ester, phenol sulfonate 2.0%, and no acetate ester or phenoxyacetic acid. The purified product so prepared had the following structure:

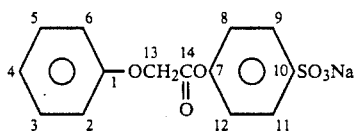

Analysis by $^{13}$C-nmr (DMSO, ppm downfield from TMS) showed only absorbances necessary for the product. Using the numbering system shown, these assignments are made: C$_{14}$ (167.9), C$_1$ (157.6), C$_7$ (150.2), C$_{10}$ (145.7), C$_{3,5}$ (129.7), C$_{9,11}$ (127.3), C$_4$ (121.6), C$_{8,12}$ (121.2), C$_{2,6}$ (114.7) and C$_{13}$ (64.7).

EXAMPLE IB

A 500 ml three-neck flask was fitted with a paddle stirrer, condenser, and then lowered into an oil bath. To the flask was added distilled water (250 ml) and sodium hydroxide (20 g, 0.5 mole) stirring until all dissolved. The 4-t-butylphenol (37.6 g, 0.25 mole) was added and stirring was continued until solution was complete. To this was added chloroatic acid (23.6 g, 0.25 mole) and the resulting solution refluxed for three hours. Hydrochloric acid (approximately 21 ml of 37.5%) was added until the pH of the solution was about one. A yellow oil then precipitated from solution and cooling the reaction flask in an ice-bath gave a yellow solid. The slurry was filtered and the yellow solid dried to give 47.3 g of material.

Thin layer chromotographic analysis of the crude material (Si-gel, Hx-ETAC, 80-20) showed a small yellow spot at Rf=0.81, a small amount of residual 4-t-butylphenol at Rf=0.51, and the product acid at Rf=0.20. The crude solid was dissolved in Hx-CH$_2$Cl$_2$ (50-50, 200 ml) and placed on a column of silica gel (200 g, 230-400 mesh, 4 cm diameter×43 cm high) packed with the same solvent mix The column was eluted with Hx-CH$_2$Cl$_2$ (55 ml), CH$_2$Cl$_2$ (600 ml), and finally Hx-ETAC (80-20, 1800 ml). Fractions from the latter column eluent were combined and the solvent evaporated to give a white solid (21.4 g). This solid had m.p. 86.5°–87.5° C. and the infrared spectrum showed a strong carbonyl at 1710 cm$^{-1}$ and absence of any hydroxyl absorption in the 3500 cm$^{-1}$ region. Analysis via titration gave a purity of 99.4%. The structure of this 4-t-butylphenoxy acetic acid intermediate is illlustrated below:

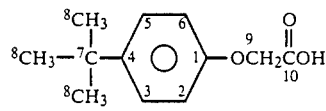

The $^{13}$C-NMR showed only those chemical shifts expected for the product. The assignments are shown in the structure: C$_1$ (155.1), C$_{2,6}$ (114.0), C$_{3,5}$ (126.2), C$_4$ (144.5), C$_7$ (33.9), C$_8$ (31.3), C$_9$ (64.7), and C$_{10}$ (174.9). The shifts are downfield from TMS in CDCl$_3$ solvent.

A 500 ml three-neck Morton flask was fitted with a paddle stirrer, condenser with drying tube, and heating mantle. Dodecane (200 ml) was added to the flask and heated to approximately 140° C. The 4-t-butylphenoxyacetic acid (15.0 g., 0.72 mole) was added with rapid stirring and after it melted, the acetic anhydride (8.0 ml, 0.085 mole), anhydrous p-phenolsulfonate (15.0 g, 0.076 mole), and sodium sulfate (0.4 g, 0.005 mole) were added. The mixture was heated with constant stirring for 18 hours.

At the end of this time, a Dean-Stark trap was inserted between the flask and condenser. The acetic acid was allowed to azeotrope out (5 hours) and the slurry cooled to room temperature. The slurry was filtered and the tan solid washed with ether (3×400 ml), and air dried on the filter pad to give 25.9 g of a light tan solid.

A portion of this solid (20.0 g) was recrystallized from MeOH-H$_2$O (50-50, 120 ml). The resulting solid was dried in a vacuum oven (110° C.) overnight to give a white solid (14.4 g). This solid showed a strong carbonyl at 1780 cm$^{-1}$ in the infrared solution Analysis by HPLC showed it to be 91.5% pure. The structure of the inventive sodium (p-phenylsulfonate)-4-t-butylphenoxyacetate is shown below:

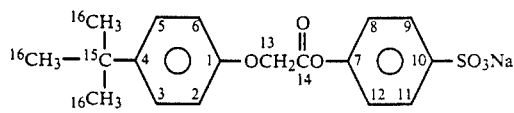

The $^{13}$C-NMR showed only those chemical shifts expected for the product. The assignments are shown in the structure: C$_1$ (155.0), C$_{2,6}$ (113.8), C$_{3,5}$ (125.8), C (143.8), C (149.6), C (120.5), C ,11 (126.7), C (145.7), C$_{13}$ (64.6), C$_{14}$ (167.4), C$_{15}$ (33.5), and C$_{16}$ (31.0). The chemical shifts are downfield from TMS in DMSO solvent.

EXAMPLE II

A 500 ml three-neck round bottom flask was equipped with paddle stirrer, condenser and drying tube and flushed with nitrogen. THF (150 ml), resorcinol (15 g), pyridine (21.4 g) and phenoxyacetyl chloride (46.5 g) were admixed and 50 ml additional THF added. The mixture was heated to about 60° C. for almost three hours. The THF was stripped off and a yellow oil recovered. The oil was dissolved in $CH_2Cl_2$ (200 ml) and placed in a one-liter L separatory funnel and extracted with 5% $Na_2CO_3$ (2×200 then washed with water (200 ml) and dried over magnesium sulfate. The magnesium sulfate was then filtered off and the solution evaporated to obtain a orange-yellow oil. After sitting for a few minutes, the oil solidified to a cream-colored solid. IR analysis showed no hydroxyl present and two carbonyls at 1780 cm$^{-1}$ and 1790 cm$^{-1}$. Thin layer chromatography (with silica gel, either $CH_2Cl_2$ or Hx-ETAC (80-20), Uv visualization) showed one spot and a small spot at the origin. A short column packed with silica gel (100 g, 200-400 mesh, 4 cm D×20 cm H) was prepared with $CH_2Cl_2$ as liquid carrier. The yellow solid, dissolved in $CH_2Cl_2$ (about 80 ml), was placed on the column and eluted to recover light yellow solid.

The solid from the column was dissolved in hot ethanol (about 300 ml), cooled in an ice bath to 15° C., and filtered. The light yellow solid was permitted to air dry and then put in a vacuum oven at 50° C. overnight. This dried material gave a melting point of 84.5°-85.5° C. Thin layer chromatography (methylene chloride, silica gel) showed only one spot ($R_f=0.52$) with no spots at the origin. IR shows no hydroxyl at all, and two carbonyls at 1790 cm$^{-1}$ and 1800 cm$^{-1}$.

Analysis by $^{13}$C-nmr (CDCl$_3$, ppm downfield from TMS), showed only the absorbances necessary for the product. Using the numbering system shown by the structure of the product, these assignments are made: $C_{14}$ (167.0), $C_7$ (157.6), $C_{1,3}$ (150.4), $C_5$ (129.8), $C_{9,11}$ (129.6), $C_{10}$ (121.9), $C_{4,6}$ (119.0), $C_2$ (114.9), $C_{8,12}$ (114.7) and $C_{13}$ (65.1). The structure of this product is illustrated as follows.

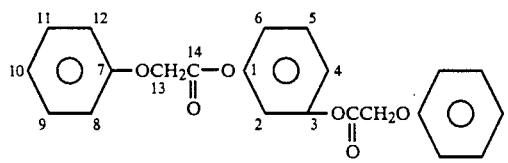

EXAMPLE III

A 500 ml three-neck flask was fitted with condenser, drying tube, paddle stirrer and flushed with nitrogen. Acetone oxime (14.6 g) and THF (100 ml) were added with stirring. Pyridine (15.8 g) was then added. Phenoxyacetyl chloride (34.1 g) was then added, as was an additional 50 ml THF. The reaction mixture was heated to 60° C. for three hours and then cooled. White solid was filtered from the cooled reaction mixture and was filtered off. The solvent was then stripped off to obtain a light golden oil. IR analysis of the oil showed a strong carbonyl at 1780 cm$^{-1}$ and no hydroxyl present.

The crude oil was purified by chromatography with Hx-ETAC (80-20) as carrier on a column of silica gel G (150 g, 230-400 mesh, 4 cm diameter×31 cm high). The Hx-ETAC was stripped off to give a solid with a melting point of 63.0°-64.0° C. IR analysis showed a very strong carbonyl at 1785 cm$^{-1}$, no hydroxyl. $^{13}$C-nmr was clean and showed only the absorbances expected for the product (CDCl$_3$, ppm downfield from TMS). Using the numbering system shown on the product structure, these assignments are made: $C_8$ (165.8), $C_9$ (164.0), $C_1$ (156.8), $C_{3,5}$ (128.5), $C_4$ (120.5), $C_{2,6}$ (113.6), $C_7$ (63.6), $C_{10}$ (20.4) and $C_{11}$ (15.5). An HPLC analysis of the product showed it to be 98.8% pure. This product has the structure illustrated below:

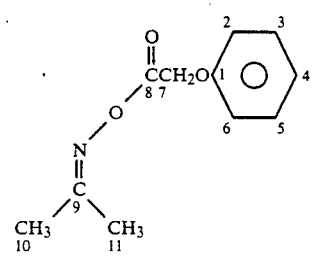

EXAMPLE IV

In a procedure analagous to that of Example III, phenoxyacetyl chloride (38.6 g), methyl ethyl ketoxime (19.7 g) and pyridine (17.8 g) were reacted in THF solvent with an oil bath of 60°-70° C. The crude product was purified by chromatography over silica gel 60 (200 g, 230-400 mesh, 4 cm diameter and 41 cm high) in 50-50 Hx-$CH_2Cl_2$. IR analysis of the purified product showed one large carbonyl at 1782 cm$^{-1}$, no sign of any hydroxyl. The $^{13}$C-nmr showed only those absorbances necessary for the product (CDCl$_3$, ppm downfield from TMS). Using the numbering system shown, these assignments are made: $C_9$ minor config. (168.7), $C_9$ major config. (167.8), $C_8$ (166.3), $C_1$ (157.0), $C_{3,5}$ (128.7), $C_4$ (120.8), $C_{2,6}$ (113.8), $C_7$ (63.9), $C_{11}$ major config. (28.4), $C_{11}$ minor config. (23.0) $C_{10}$ minor config. (18.4), $C_{10}$ major config. (14.0), $C_{12}$ major config. (9.7) and $C_{12}$ minor config. (9.2). The minor and major structural configurations of this product are illustrated below:

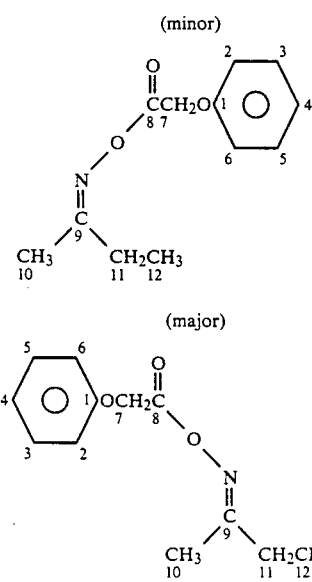

EXAMPLE V

In a 500 ml three-neck flask fitted with paddle stirrer, condenser and drying tubes are added n-hydroxysuccinimide (11.5 g), phenoxyacetyl chloride (17.0 g) and pyridine (7.9 g) in about 250 ml THF. The reaction mixture is heated for about three hours at 60° C. As with the crude products of Examples III and IV, this crude product may also be purified with a silica gel column using a $CH_2Cl_2$ solution. The structure of this product is illustrated as follows:

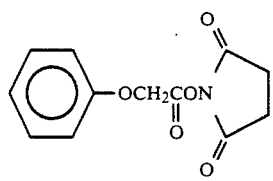

EXAMPLE VI

A 500 ml three-neck flask is fitted with paddle stirrer, condenser and drying tube. N-hydroxyphthalimide (16.3 g), pyridine (7.9 g) and phenoxyacetyl chloride (17.0 g) are reacted in 250 ml THF solvent in an analogous manner to Example v. The crude reaction product may be purified over a silica gel column. The structure of the resultant product is illustrated below:

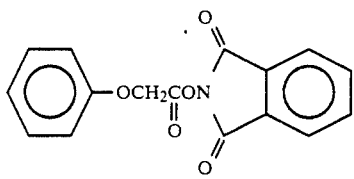

EXAMPLE VII

A 500 ml three-neck flask was fitted with a paddle stirrer, drying tube and flushed with nitrogen To the flask is added THF (150 ml) and 4-phenylpyridine N-oxide (5 g). A light yellow solution results. To this is added rapidly phenoxyacetyl chloride (4.9 g) in THF (20 ml). The mixture is stirred very rapidly for about 1½ minutes. A gelatinous precipitate forms almost immediately. When the viscous solution is diluted with ether (less than 300 ml), a white solid layer separates. The mix is filtered to give a white solid, which is washed with ether and dried. The structure of the product is illustrated as follows:

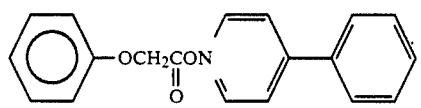

While the invention has been described in connection with specific embodiments thereof, it will be understood that it is capable of further-modifications, and this application is intended to cover any variations, uses or adaptations of the invention following, in general, the principles of the invention and including such departures from the disclosure as come within the known or customary practice in the art to which the invention pertains and as may be applied to the essential features hereinbefore set forth, and as fall within the scope of the invention and the limits of the appended claims.

We claim:

1. A peroxyacid precursor having the structure

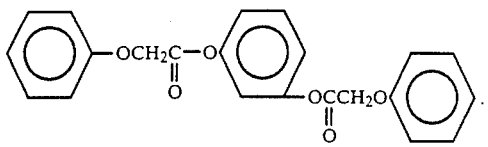

2. A peroxyacid precursor having the structure

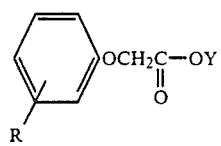

wherein R is hydrogen or an alkyl of not more than 5 carbons, and Y is a substituted or unsubstituted aromatic ring.

3. The peroxygen precursor as in claim 2 wherein the substituent of the aromatic ring is one or more of a sulfate, a carbonate, a quaternary nitrogen, an alkoxy of about 1 to 10 carbons, or an alkyl of about 1 to 6 carbons and can additionally include a sulfonate on the ring.

4. A peroxyacid precursor having the structure

wherein R is hydrogen or an alkyl of not more than 5 carbons and Z is derived from an oxime, an N-hydroxyimide, or an amine oxide.

5. The peroxygen precursor as in claim 4 having the structure

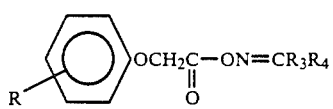

wherein R is hydrogen or an alkyl of not more than 5 carbons and $R_3$ and $R_4$ are each straight or branched chain alkyl with 1 to 6 carbons, an aryl or a cycloalkyl.

6. The peroxyacid precursor as in claim 4 having the structure

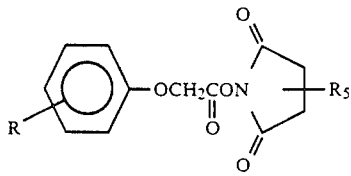

or

-continued

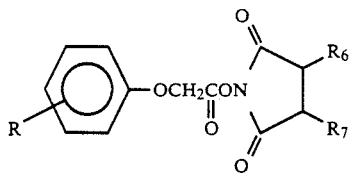

wherein where R is hydrogen or an alkyl of not more than 5 carbons, $R_5$ is hydrogen or an aromatic ring, and $R_6$ and $R_7$ are straight or branched hydrocarbons with about 1 to 6 carbons.

7. The peroxyacid precursor as in claim 4 having the structure

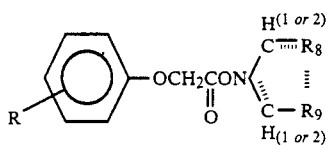

wherein where R is hydrogen or an alkyl of not more than 5 carbons and $R_8$ and $R_9$ are alkyl, aryl or alkylaryl with about 1 to 20 carbons and may be part of the same aromatic or cycloalkyl ring.

8. The peroxygen precursor as in claim 2 or 4 coated with a surfactant.

9. A peroxygen precursor having the structure

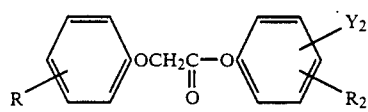

wherein $R_2$ is hydrogen, a straight or branched alkyl with about 1-6 carbons or an alkoxy with about 1-10 carbons, and $Y_2$ is a sulfate, a carbonate, or a quaternary nitrogen.

10. A peroxyacid precursor including at least one α-substituted carbonyl moiety with the structure

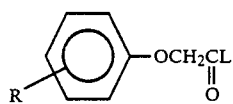

wherein R is hydrogen or an alkyl with not more than 5 carbons and L is a group whose conjugate acid has a pKa in aqueous solution of between about 5 to about 13, wherein L is selected from the group consisting of (a) 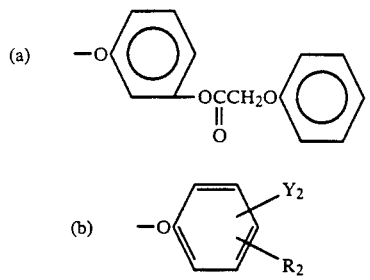

(b)

wherein $R_2$ is hydrogen, a straight or branched alkyl with about 1-6 carbons or an alkoxy with about 1-10 carbons, and $Y_2$ is a sulfate, a carbonate, or a quaternary nitrogen;

(c) $-ON=CR_3R_4$ wherein $R_3$ and $R_4$ are each straight or branched chain alkyl with 1 to 6 carbons, an aryl or a cycloaryl;

(d) 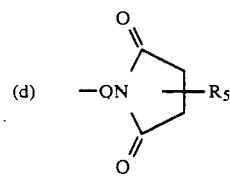

wherein $R_5$ is hydrogen or an aromatic ring;

(e) 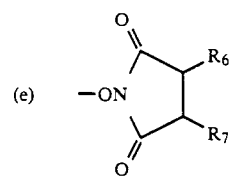

wherein $R_6$ and $R_7$ are straight or branched hydrocarbons with about 1 to 6 carbons; and, (f) 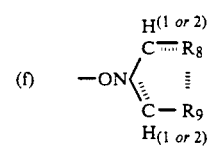

wherein $R_8$ and $R_9$ are alkyl, aryl, or alkylaryl with about 1 to 20 carbons and may be part of the same aromatic or cycloalkyl ring.

11. The precursor as in claim 10 coated with a surfactant.

12. The precursor as in claim 10 wherein the precursor is in granular form, and a surfactant is coated on granules thereof.

* * * * *

UNITED STATES PATENT AND TRADEMARK OFFICE
CERTIFICATE OF CORRECTION

PATENT NO. : 5,049,305

DATED     : SEPTEMBER 17, 1991

INVENTOR(S) : Alfred G. Zielske, Ronald A. Fong

It is certified that error appears in the above-identified patent and that said Letters Patent is hereby corrected as shown below:

Title Page of Patent          insert --[73] Assignee: The Clorox
                              Company, Oakland, California Signed and Sealed this Fourth Day of January, 1994

Attest:

BRUCE LEHMAN

*Attesting Officer*          Commissioner of Patents and Trademarks